(12) United States Patent
Carter

(10) Patent No.: US 9,463,211 B2
(45) Date of Patent: *Oct. 11, 2016

(54) SKIN SALVE FOR TREATING INTERTRIGO

(71) Applicant: Teresa D. Carter, Barberton, OH (US)

(72) Inventor: Teresa D. Carter, Barberton, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/936,779

(22) Filed: Nov. 10, 2015

(65) Prior Publication Data

US 2016/0058815 A1 Mar. 3, 2016

Related U.S. Application Data

(60) Continuation of application No. 14/452,009, filed on Aug. 5, 2014, now Pat. No. 9,180,146, which is a division of application No. 12/286,582, filed on Oct. 1, 2008, now Pat. No. 8,795,735.

(60) Provisional application No. 60/997,066, filed on Oct. 1, 2007.

(51) Int. Cl.

| | |
|---|---|
| *A61K 36/534* | (2006.01) |
| *A61K 35/64* | (2015.01) |
| *A61K 36/61* | (2006.01) |
| *A61K 35/644* | (2015.01) |
| *A61K 9/00* | (2006.01) |
| *A61K 9/06* | (2006.01) |
| *A61K 35/06* | (2006.01) |

(52) U.S. Cl.
CPC ............. *A61K 36/61* (2013.01); *A61K 9/0014* (2013.01); *A61K 9/06* (2013.01); *A61K 35/06* (2013.01); *A61K 35/644* (2013.01); *A61K 36/534* (2013.01)

(58) Field of Classification Search
CPC ............................. A61K 36/534; A61K 35/64
USPC .................................................. 424/539, 747
See application file for complete search history.

(56) References Cited

U.S. PATENT DOCUMENTS

| | | | | |
|---|---|---|---|---|
| 2002/0182260 A1* | 12/2002 | Mak | ...................... | A61K 36/00 424/522 |
| 2004/0127385 A1* | 7/2004 | O'Neil | ................... | A01N 65/00 510/438 |

* cited by examiner

*Primary Examiner* — Chris R Tate
*Assistant Examiner* — Deborah Davis
(74) *Attorney, Agent, or Firm* — Alvin T. Rockhill

(57) ABSTRACT

The subject patent discloses a method for treating intertrigo on the underside of a female breasts which comprises (1) applying a skin salve to the underside of the female breasts, wherein the female breasts are dry, and wherein the skin salve is comprised of (i) petrolatum, (ii) from 11 weight percent to 60 weight percent beeswax, and (iii) from 0.25 weight percent to 10 weight percent peppermint oil, wherein the skin salve has a viscosity at 25° C. which is within the range of 11 Pa·s to 15 Pa·s at a shear rate of 35 l/s, and (2) allowing the skin salve to remain in contact with female breasts for a period of at least 4 hours.

19 Claims, No Drawings

SKIN SALVE FOR TREATING INTERTRIGO

This is a continuation of U.S. patent application Ser. No. 14/452,009, filed on Aug. 5, 2014, which is a divisional of U.S. patent application Ser. No. 12/286,582, filed on Oct. 1, 2008, now issued as U.S. Pat. No. 8,795,735 B1, which claims the benefit of U.S. Provisional Patent Application Ser. No. 60/997,066, filed on Oct. 1, 2007. The teachings of U.S. patent application Ser. No. 14/452,009, U.S. patent application Ser. No. 12/286,582 and U.S. Provisional Patent Application Ser. No. 60/997,066 are incorporated herein by reference in their entirety.

BACKGROUND OF THE INVENTION

Intertrigo is an unsightly inflammation of skin that typically develops at the site of body folds due to chafing of warm, moist skin. It typically causes discomfort in the form of itching and burning. Intertrigo usually occurs on the underside of the breasts of women and is more prevalent in the case of women having large breasts. However, intertrigo can also develop in other areas where body folds cause the skin to remain warm and moist for prolonged periods. For instance, intertrigo sometimes also develops on areas of the inner thighs, the armpits, the underside of the belly, behind the ears, and the web spaces between the toes and fingers.

It is normally difficult to cure intertrigo or to alleviate its symptoms. In fact, some people have continuously suffered from intertrigo over a period of many years. There is accordingly a need for a simple, safe, and cost effective cure for this malady.

SUMMARY OF THE INVENTION

The skin salve of this invention is highly effective for utilization in treating intertrigo and a variety of other skin maladies, such as scabies, psoriasis and eczema. In general it is useful in the treatment of most types of skin irritation and skin rashes.

The present invention more specifically discloses a skin salve that is comprised of (1) petrolatum, (2) beeswax, and (3) peppermint oil, wherein the beeswax is present in said salve at a level of at least 11 weight percent. For most applications, it is desirable for the skin salve of this invention to contain only (1) petrolatum, (2) beeswax, and (3) peppermint oil. However, in some other cases it is desirable for the skin salve of this invention to consist of (1) petrolatum, (2) beeswax, and (3) peppermint oil, and optionally mineral oil, grape seed oil, castor oil, one or more vegetable oils, glycerin, and vitamin E.

The subject invention also reveals a method for treating irritated skin which comprised topically applying a skin salve to the irritated skin, wherein the skin salve is comprised of (1) petrolatum, (2) beeswax, and (3) peppermint oil, wherein the beeswax is present in said salve at a level of at least 11 weight percent. The skin salve of this invention will typically be allowed to remain in contact with the irritated skin for at least 4 hours, preferably at least 8 hours, and most preferably at least 10 hours.

The present invention further discloses a method for treating intertrigo on the underside of female breasts which comprises (1) soaking the female breasts in warm water, (2) drying the female breasts, (3) applying the skin salve of claim 1 to the underside of the dried female breasts, and (3) allowing the skin salve to remain in contact with female breasts for a period of at least 4 hours.

DETAILED DESCRIPTION OF THE INVENTION

The skin salve of this invention is a mixture of (1) petrolatum, (2) beeswax, and (3) peppermint oil. To attain the needed viscosity to be highly effective it is critical for the skin salve of this invention to contain at least 11 weight percent of the beeswax. The skin salve of this invention will typically contain from 11 to 60 weight percent beeswax. For most applications, it is desirable for the skin salve of this invention to contain only (1) petrolatum, (2) beeswax, and (3) peppermint oil. However, in some other cases it is desirable for the skin salve of this invention to consist of (1) petrolatum, (2) beeswax, and (3) peppermint oil, and (4) optionally mineral oil, grape seed oil, castor oil, one or more vegetable oils, glycerin, and vitamin E. In such cases the amount of optional ingredients in addition to the (1) petrolatum, (2) beeswax, and (3) peppermint oil will total less than one percent by weight, base upon the total weight of the salve. The total amount of mineral oil, grape seed oil, castor oil, vegetable oils, glycerin, and vitamin E present in the salve will preferably total less than 0.025 weight percent of the total weight of the salve. The total amount of mineral oil, grape seed oil, castor oil, vegetable oils, glycerin, and vitamin E present in the salve will more preferably total less than 0.01 weight percent of the total weight of the salve. The total amount of mineral oil, grape seed oil, castor oil, vegetable oils, glycerin, and vitamin E present in the salve will most preferably total less than 0.001 weight percent of the total weight of the salve.

In one embodiment of this invention the skin salve is further comprised of tea tree oil. Tea tree oil is a very pale golden colored essential oil that is recovered from the leaves of *Melaleuca alternifolia* trees. In this case the skin salve is comprised of (1) petrolatum, (2) beeswax, (3) peppermint oil, and (4) tea tree oil. In still another embodiment of this invention the skin salve is comprised of (1) petrolatum, (2) beeswax, (3) peppermint oil, and (4) terpinen-4-ol. It is frequently desirable for the skin salve to consist of (1) petrolatum, (2) beeswax, (3) peppermint oil, and (4) tea tree oil or terpinen-4-ol. However, the skin salve can consist of (1) petrolatum, (2) beeswax, (3) peppermint oil, (4) tea tree oil or terpinen-4-ol, and (5) optionally, mineral oil, grape seed oil, castor oil, one or more vegetable oils, glycerin, and vitamin E. The tea tree oil will typically be included in such compositions at a level which is within the range of 0.1 weight percent to 5 weight percent, based upon the total weight of the salve. The tea tree oil will more typically be present in the salve at a level which is within the range of 0.25 weight percent to 2 weight percent and will preferably be present at a level which is within the range of 0.5 weight percent to 1 weight percent.

The skin salve of this invention can contain up to about 1 weight percent of at least one oil selected from the group consisting of shea butter, soy oil, almond oil, eucalyptus essential oil, olive oil, coconut oil, corn oil, caster oil, mineral oil, soybean oil, canola oil, rapeseed oil, cottonseed oil, palm oil, sesame oil, sunflower oil, safflower oil, rice bran oil, borage seed oil, *syzigium aromaticum* oil, hempseed oil, herring oil, cod-liver oil, salmon oil, flaxseed oil, rape seed oil, evening primrose oil, rosehip oil, tea tree oil, *melaleuca* oil and jojova oil. However, the skin salve of this invention will typically be void of such oils. The skin salve of this invention can also contain zinc oxide, boric acid, Vitamin A, Vitamin E, and a paraffin wax.

The skin salve of this invention will typically be void of water and hydrophilic compounds. It is believed that ethyl alcohol, isopropyl alcohol, n-propyl alcohol, n-butyl alcohol, isobutyl alcohol, tertiary butyl alcohol, glycerin, lecithin, aloe extract, and lavender oil interfere with the functionality of the skin salves of this invention. Accordingly, the skin salves of this invention are typically also void of ethyl alcohol, isopropyl alcohol, n-propyl alcohol, n-butyl alcohol, isobutyl alcohol, tertiary butyl alcohol, glycerin, lecithin, aloe extract, and lavender oil.

The skin salve of this invention will normally contain at least 0.25 weight percent peppermint oil and typically contain from 0.25 weight percent to 10 weight percent peppermint oil, based upon the total weight of the skin salve. The skin salve of this invention will more typically contain from 0.5 weight percent to 6 weight percent peppermint oil. The skin salve of this invention will preferably contain from 1 weight percent to 5 weight percent peppermint oil and will more preferably contain from 1 weight percent to 3 weight percent peppermint oil. The skin salve of this invention will most preferably contain from 1.2 weight percent to 2 weight percent peppermint oil and will commonly contain from 1.4 weight percent to 1.8 weight percent peppermint oil.

The skin salve of this invention will normally contain at least 0.25 weight percent beeswax and typically contain from 11 weight percent to 60 weight percent bees wax, based upon the total weight of the skin salve. The skin salve of this invention will more typically contain from 12 weight percent to 45 weight percent beeswax. The skin salve of this invention will generally contain from 12 weight percent to 30 weight percent beeswax and will preferably contain from 12 weight percent to 20 weight percent beeswax. The skin salve of this invention will more preferably contain from 14 weight percent to 18 weight percent beeswax and will most preferably contain from 16 weight percent to 18 weight percent beeswax.

It is important for the skin salve of this invention to be of a high viscosity to attain the desired results. The beeswax will typically be included at a level which is sufficient to result in the skin salve having a viscosity at 25° C. which is within the range of 11 Pa·s to 15 Pa·s at a shear rate of 35 l/s. The skin salve will preferably have a viscosity at 25° C. which is within the range of 12 Pa·s to 14 Pa·s at a shear rate of 35 l/s. The skin salve will more preferably have a viscosity at 25° C. that is within the range of 13.2 Pa·s to 13.8 Pa·s at a shear rate of 35 l/s. The skin salve will typically have a viscosity at 25° C. that is within the range of 8 Pa·s to 12 Pa·s at a shear rate of 50 l/s. The skin salve will preferably have a viscosity at 25° C. which is within the range of 9 Pa·s to 11.5 Pa·s at a shear rate of 50 l/s. The skin salve will more preferably have a viscosity at 25° C. that is within the range of 10.2 Pa·s to 11.0 Pa·s at a shear rate of 50 l/s. The skin salve will typically have a viscosity at 38° C. that is within the range of 2.0 Pa·s to 2.6 Pa·s at a shear rate of 35 l/s. The skin salve will preferably have a viscosity at 38° C. which is within the range of 2.1 Pa·s to 2.5 Pa·s at a shear rate of 35 l/s. The skin salve will more preferably have a viscosity at 38° C. that is within the range of 2.2 Pa·s to 2.4 Pa·s at a shear rate of 35 l/s. The skin salve will typically have a viscosity at 50° C. that is within the range of 0.200 Pa·s to 0.240 Pa·s at a shear rate of 50 l/s. The skin salve will preferably have a viscosity at 50° C. which is within the range of 0.210 Pa·s to 0.230 Pa·s at a shear rate of 50 l/s. The skin salve will more preferably have a viscosity at 50° C. that is within the range of 0.215 Pa·s to 0.220 Pa·s at a shear rate of 50 l/s.

The skin salve of this invention is made by simply mixing the petrolatum, the beeswax, the peppermint oil and additional desired ingredients at an elevated temperature which is sufficient to melt the beeswax. The mixing will be carried out until a uniform, homogeneous mixture is attained.

This invention is illustrated by the following examples that are merely for the purpose of illustration and are not to be regarded as limiting the scope of the invention or the manner in which it can be practiced. Unless specifically indicated otherwise, parts and percentages are given by weight.

Example 1

In this experiment the skin salve of this invention was made by putting 36 ounces of petroleum jelly, 7.4 ounces of beeswax, and 0.7 ounces of peppermint oil in an open pot. The pot was then heated to a temperature that was sufficient to completely melt the mixture of petroleum jelly, beeswax, and peppermint oil. Then the mixture was stirred while molten to attain a homogeneous mixture. Then the mixture was allowed to cool to ambient temperature. After cooling the skin salve made was placed into small jars.

The viscosity of the skin salve made in this experiment was measured in an Anton Paar (Model Physica MCR 310) viscometer having a concentric cylinder shearing geometry which was operated under continuous shear (not rotating). Its viscosity at 25° C. was determined to be 13.4 Pa·s at a shear rate of 35 l/s and 10.6 Pa·s at a shear rate of 50 l/s. Its viscosity at 38° C. was determined to be 2.32 Pa·s at a shear rate of 35 l/s and 1.99 Pa·s at a shear rate of 50 l/s. Its viscosity at 50° C. was determined to be 0.257 Pa·s at a shear rate of 35 l/s and 0.219 Pa·s at a shear rate of 50 l/s.

Example 2

In this experiment the skin salve made in Example 1 was evaluated on a 45 year old woman suffering from diabetes and intertrigo on the underside of her breasts. The intertrigo had caused the skin to be inflamed, burned, and was raw in some areas. This skin condition was painful and was aggravated by the patient's bra, heat, and sweat. Additionally, the intertrigo was an unsightly rash.

This patient had treated her intertrigo with a variety of over-the-counter salves and powders without success. Additionally, this patient had treated the intertrigo with isopropyl alcohol without any relief.

This patient topically applied the skin salve of this invention which was made by the procedure described in Example 1 to the inflamed skin under her breasts on two consecutive evenings after taking a bath. This completely alleviated the intertrigo. The skin under her breasts returned to normal and no longer burned or caused any other type of discomfort. This patient has remained free of intertrigo for over four months without the need for reapplication of the skin salve of this invention.

Example 3

In this experiment the skin salve made in Example 1 was evaluated on another Caucasian woman suffering from diabetes and intertrigo on the underside of her breasts. This woman was about 50 years of age and had suffered from intertrigo continuously for over 15 years. The intertrigo had caused the skin to be inflamed, burned, and was raw in some areas. This skin condition was painful and was aggravated by the patient's bra, heat, and sweat. Additionally, the intertrigo was an unsightly rash that had caused scar tissue to develop over the years.

This patient topically applied the skin salve of this invention which was made by the procedure described in Example 1 to the inflamed skin under her breasts on two consecutive evenings after taking a bath. This completely alleviated the intertrigo. The skin under her breasts returned to normal and no longer burned or caused any other type of discomfort. However, the scars that had developed over the years as a result of the intertrigo remained. This patient has been free of intertrigo for over four months without the need for reapplication of the skin salve of this invention.

Example 4

In this experiment the skin salve made in Example 1 was evaluated on another Caucasian woman suffering from intertrigo on the underside of her breasts. This woman was about 28 years of age and had suffered from intertrigo continuously since her breasts developed as a teenager. The intertrigo had caused the skin to be inflamed, burned, and was raw in some areas. This skin condition was painful and was aggravated by the patient's bra, heat, and sweat. Additionally, the intertrigo was an unsightly rash that had caused scar tissue to develop over the years.

This patient topically applied the skin salve of this invention which was made by the procedure described in Example 1 to the inflamed skin under her breasts on one evening after taking a bath. This completely alleviated the intertrigo. The skin under her breasts returned to normal and no longer burned or caused any other type of discomfort. However, the scars that had developed over the years as a result of the intertrigo remained. This patient has been free of intertrigo for over four months without the need for reapplication of the skin salve of this invention.

Example 5

In this experiment the skin salve made in Example 1 was evaluated on an African American woman suffering from intertrigo on the underside of her breasts. This woman was about 48 years of age and had suffered from intertrigo continuously for many months. The intertrigo had caused the skin to be inflamed, burned, and was raw in some areas. This skin condition was painful and was aggravated by the patient's bra, heat, and sweat.

This patient topically applied the skin salve of this invention which was made by the procedure described in Example 1 to the inflamed skin under her breasts on one evening after taking a bath. This completely alleviated the intertrigo. The skin under her breasts returned to normal and no longer burned or caused any other type of discomfort. However, the scars that had developed over the years as a result of the intertrigo remained. This patient has been free of intertrigo for over four months without the need for reapplication of the skin salve of this invention.

Example 6

In this experiment the skin salve made in Example 1 was evaluated on an African American woman suffering from intertrigo on the underside of her breasts and the underside of her belly. This woman was about 23 years of age and had suffered from intertrigo continuously for many months. The intertrigo had caused the skin to be inflamed, burned, and was raw in some areas. This skin condition was painful and was aggravated by the patient's bra, heat, and sweat.

This patient topically applied the skin salve of this invention which was made by the procedure described in Example 1 to the inflamed skin under her breasts on one evening after taking a bath. This completely alleviated the intertrigo under her breasts and under her belly. The skin under her breasts and belly returned to normal and no longer burned or caused any other type of discomfort. This patient has been free of intertrigo for a month without the need for reapplication of the skin salve of this invention.

Example 7

In this experiment the skin salve made in Example 1 was evaluated on an African American woman suffering from intertrigo on the underside of her breasts. This woman was about 65 years of age and had suffered from intertrigo continuously for many months. The intertrigo had caused the skin to be inflamed, burned, and was raw in some areas. This skin condition was painful and was aggravated by the patient's bra, heat, and sweat.

This patient topically applied the skin salve of this invention which was made by the procedure described in Example 1 to the inflamed skin under her breasts on one evening after taking a bath. This completely alleviated the intertrigo under her breasts. The skin under her breasts returned to normal and no longer burned or caused any other type of discomfort. This patient has been free of intertrigo for over three months without the need for reapplication of the skin salve of this invention.

Example 8

In this experiment the skin salve made in Example 1 was evaluated on another Caucasian woman suffering from intertrigo on the underside of her breasts. This woman was about 35 years of age and had suffered from intertrigo continuously for many months. The intertrigo had caused the skin to be inflamed, burned, and was raw in some areas. This skin condition was painful and was aggravated by the patient's bra, heat, and sweat. Additionally, the intertrigo was an unsightly rash that had caused scar tissue to develop over the years.

This patient topically applied the skin salve of this invention which was made by the procedure described in Example 1 to the inflamed skin under her breasts on two consecutive evenings after taking a bath. This completely alleviated the intertrigo. The skin under her breasts returned to normal and no longer burned or caused any other type of discomfort. This patient has been free of intertrigo for over three months without the need for reapplication of the skin salve of this invention.

Example 9

In this experiment the skin salve made in Example 1 was evaluated on a 6 year old boy suffering from a rash on his buttocks. The skin salve of this invention which was made by the procedure described in Example 1 was applied to the skin rash on this patient after he was given a warm bath. This completely alleviated the rash. The young boy has remained rash free for over three weeks without the need for reapplication of the skin salve of this invention.

This young boy also suffered from a painful skin lesion on bottom of his ear. The skin salve of this invention was also applied to this lesion on his ear on three consecutive days. The lesion quickly healed.

Example 10

In this experiment the skin salve made in Example 1 was evaluated on a 21 month old African American baby suffering from a rash on his buttocks and eczema on the inside of his right arm. This baby has previously been treated with prescription drugs dispensed by a physician. However, the prescription drugs were not effective and did not cure or alleviate this skin rash or the eczema.

The skin salve of this invention which was made by the procedure described in Example 1 was applied to the skin rash on this patient. One application of the skin salve of this invention completely alleviated the rash.

Example 11

In this experiment the skin salve made in Example 1 was evaluated on a 10 year old Caucasian boy suffering from an itchy skin rash in his crotch area. A salve containing 1.9 weight percent peppermint oil in petroleum jelly was applied to the skin rash on two consecutive days. However, this did not cure or alleviate the itchy skin rash.

The skin salve of this invention which was made by the procedure described in Example 1 was subsequently applied to the skin rash on this young boy. This quickly and completely alleviated the itchy rash.

Example 12

In this experiment the skin salve made in Example 1 was evaluated on a 28 year old woman that was suffering from a spider bite. It was applied to the skin of the woman in the area of the bite. This initially burned, but quickly provided lasting relief.

Example 13

In this experiment the skin salve made in Example 1 was evaluated on a 43 year old woman that was suffering from flea bites. It was applied to the skin of the woman in the area of the bites. The application of the skin salve of this invention quickly provided lasting relief.

Example 14

In this experiment the skin salve made in Example 1 was evaluated on a 70 year old Caucasian woman that was diagnosed by a physician as having scabies caused by parasitic mites and psoriasis. The woman also had diabetes. Over nine months of treatment with prescription drugs was not effective in curing or alleviating the scabies or psoriasis from which this woman was suffering.

This patient topically applied the skin salve of this invention to the scabies/psoriasis inflamed skin once a day for a period of six consecutive days. This completely alleviated the scabies and psoriasis from which she was suffering.

Example 15

In this experiment the skin salve made in Example 1 was evaluated on a 45 year old obese man that was suffering from intertrigo on the underside of his arms, belly, and crotch area. The intertrigo had caused the skin to be inflamed, burned, and was raw in some areas. This skin condition was painful and unsightly.

This patient topically applied the skin salve of this invention to his inflamed skin on one occasion. This completely alleviated the intertrigo. His skin returned to normal and no longer burned or caused any other type of discomfort.

Example 16

In this experiment the skin salve made in Example 1 was evaluated on a 47 year old woman that was suffering from intertrigo between her toes. The intertrigo had caused the skin to be inflamed and burned. This patient topically applied the skin salve of this invention to the skin between her toes on only one occasion. This completely alleviated the intertrigo.

Example 17

In this experiment the skin salve made in Example 1 was evaluated on a 48 year old woman that was suffering from intertrigo between her feet. The intertrigo had caused the skin to be inflamed and burned. This patient topically applied the skin salve of this invention to her feet on only one occasion. This completely alleviated the intertrigo.

Example 18

In this experiment the skin salve made in Example 1 was evaluated on a 45 year old woman that was suffering from outward hemorrhoids. This patient topically applied the skin salve of this invention to her hemorrhoids one time. This causes the burning, swelling and irritation associated with the hemorrhoids to quickly dissipate and for the hemorrhoid to retract within a period of one day. However, the hemorrhoids returned in about one week after the initial application of the skin salve of this invention. The skin salve was then reapplied to the hemorrhoids which again immediately dissipated along with the associated burning, swelling and irritation. Accordingly, the skin salve of this invention offers immediate and effective relief for the treatment of hemorrhoids.

While certain representative embodiments and details have been shown for the purpose of illustrating the subject invention, it will be apparent to those skilled in this art that various changes and modifications can be made therein without departing from the scope of the subject invention.

What is claimed is:

1. A method for treating intertrigo on the underside of a female's breasts which comprises (1) applying a skin salve to the underside of the female breasts, wherein the female's breasts are dry, and wherein the skin salve is comprised of (i) petrolatum, (ii) from 11 weight percent to 60 weight percent beeswax, and (iii) from 0.25 weight percent to 10 weight percent peppermint oil, wherein the skin salve has a viscosity at 25° C. which is within the range of 11 Pa·s to 15 Pa·s at a shear rate of 35 1/s, and (2) allowing the skin salve to remain in contact with the female's breasts for a period of at least 4 hours.

2. The method according to claim 1 wherein the skin salve is void of water.

3. The method according to claim 1 wherein the beeswax is present in said salve at a level which is within the range of 12 weight percent to 20 weight percent.

4. The method according to claim 3 wherein the peppermint oil is present in said salve at a level which is within the range of 1 weight percent to 3 weight percent.

5. The method according to claim 1 wherein the beeswax is present in said salve at a level which is within the range of 14 weight percent to 18 weight percent.

6. The method according to claim 5 wherein the peppermint oil is present in said salve at a level which is within the range of 1.2 weight percent to 2 weight percent.

7. The method according to claim 1 wherein the beeswax is present in said salve at a level which is within the range of 16 weight percent to 18 weight percent.

8. The method according to claim 7 wherein the peppermint oil is present in said salve at a level which is within the range of 1.4 weight percent to 1.8 weight percent.

9. The method according to claim 1 wherein said skin salve is void of hydrophilic compounds.

10. The method according to claim 1 wherein the skin salve consists of the petrolatum, the bees wax and the peppermint oil.

11. The method according to claim 1 wherein the skin salve further comprising of tea tree oil.

12. A skin salve comprising (1) petrolatum, (2) from 11 weight percent to 60 weight percent beeswax, and (3) from 0.25 weight percent to 10 weight percent peppermint oil, wherein the skin salve has a viscosity at 25° C. which is within the range of 8 Pa·s to 12 Pa·s at a shear rate of 50 l/s.

13. The skin salve according to claim 12 wherein the beeswax is present in said salve at a level which is within the range of 12 weight percent to 20 weight percent.

14. The skin salve according to claim 13 wherein the peppermint oil is present in said salve at a level which is within the range of 1 weight percent to 3 weight percent.

15. The skin salve according to claim 12 wherein the beeswax is present in said salve at a level which is within the range of 14 weight percent to 18 weight percent.

16. The skin salve according to claim 15 wherein the peppermint oil is present in said salve at a level which is within the range of 1.2 weight percent to 2 weight percent.

17. The skin salve according to claim 12 wherein the beeswax is present in said salve at a level which is within the range of 16 weight percent to 18 weight percent.

18. The skin salve according to claim 17 wherein the peppermint oil is present in said salve at a level which is within the range of 1.4 weight percent to 1.8 weight percent.

19. The skin salve according to claim 1 wherein said skin salve is void of water and hydrophilic compounds.

* * * * *